United States Patent
Den Boef et al.

(10) Patent No.: US 9,081,302 B2
(45) Date of Patent: Jul. 14, 2015

(54) INSPECTION APPARATUS AND METHOD, LITHOGRAPHIC APPARATUS AND LITHOGRAPHIC PROCESSING CELL

(75) Inventors: Arie Jeffrey Den Boef, Waalre (NL); Laurent Khuat Duy, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 978 days.

(21) Appl. No.: 13/228,810

(22) Filed: Sep. 9, 2011

(65) Prior Publication Data
US 2012/0075601 A1    Mar. 29, 2012

Related U.S. Application Data

(60) Provisional application No. 61/387,742, filed on Sep. 29, 2010.

(51) Int. Cl.
| | |
|---|---|
| G03B 27/54 | (2006.01) |
| G03B 27/42 | (2006.01) |
| G03F 7/20 | (2006.01) |
| G01N 21/47 | (2006.01) |
| G01N 21/55 | (2014.01) |

(52) U.S. Cl.
CPC .......... *G03F 7/70616* (2013.01); *G01N 21/47* (2013.01); *G01N 21/55* (2013.01)

(58) Field of Classification Search
CPC ... G01N 21/47; G01N 21/55; G01N 21/4704; G03F 7/70616
USPC ..................................................... 355/67, 53
See application file for complete search history.

(56) References Cited

U.S. PATENT DOCUMENTS

| | | | |
|---|---|---|---|
| 7,701,577 B2 | 4/2010 | Straaijer et al. | |
| 2004/0085544 A1 | 5/2004 | De Groot | |
| 2005/0190372 A1* | 9/2005 | Dogariu | 356/479 |
| 2009/0286172 A1* | 11/2009 | Sentoku et al. | 430/30 |

FOREIGN PATENT DOCUMENTS

EP    1 628 164 A2    2/2006

OTHER PUBLICATIONS

Leitgeb, R. A., et al., "Ultrahigh resolution Fourier domain optical coherence tomography," Optics Express, vol. 12, No. 10, May 17, 2004; pp. 2156-2165.

\* cited by examiner

*Primary Examiner* — Peter B Kim
(74) *Attorney, Agent, or Firm* — Sterne, Kessler, Goldstein & Fox P.L.L.C.

(57) ABSTRACT

An "angle-resolved" version of FD-OCT is used to measure reflectance properties. An inspection apparatus comprises an illumination source configured to provide an illumination beam, an interferometer configured to use the illumination beam to illuminate a target on a substrate at an incidence angle and to use radiation reflected from the substrate with a reference beam derived from the illumination beam to produce an output beam, a sampling device arranged to select a portion of the output beam, a spectrometer configured to receive the selected portion of the output beam and to measure a spectrum of the received selected portion of the output beam, and a processor configured to determine from the measured spectrum reflectance properties of the target such as raw spectrometer spectral data, the Fourier transformed data, the extracted intensity components or carrier phase or the calculated complex reflectance.

20 Claims, 7 Drawing Sheets

INSPECTION APPARATUS AND METHOD, LITHOGRAPHIC APPARATUS AND LITHOGRAPHIC PROCESSING CELL

CROSS REFERENCE TO RELATED APPLICATIONS

This application claims benefit under 35 U.S.C. §119(e) to U.S. Provisional Application No. 61/387,742, filed Sep. 29, 2010, which is incorporated by reference herein in its entirety.

FIELD OF THE INVENTION

The present invention relates to inspection apparatus and methods of inspection usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Critical Dimension (CD) metrology using scatterometry is done in the following ways:

1. Angle-Resolved using a selectable wavelength, however measuring on small in-die targets is challenging since the angular divergence of the light limits the angular resolution.
2. Spectroscopic using a fixed angle of incidence, however it is difficult to underfill a small target with a well-defined angle of incidence.

In both cases all measurement light must be focused into the target which is usually referred to as "underfilling the target"

SUMMARY

According to an embodiment of the present invention, there is provided an inspection apparatus comprising an illumination source configured to provide an illumination beam of broadband radiation, an interferometer configured to use the illumination beam to illuminate a target on a substrate at an incidence angle and to use radiation reflected from the substrate with a reference beam derived from the illumination beam to produce an output beam, a sampling device arranged to select a portion of the output beam, a spectrometer configured to receive the selected portion of the output beam and to measure a spectrum of the received selected portion of the output beam, and a processor configured to determine reflectance properties of the target at the incidence angle from the measured spectrum.

According to another embodiment of the present invention, there is provided an inspection method comprising the following steps. Providing an illumination beam of broadband radiation. Using the illumination beam to illuminate a target on a substrate at an incidence angle and using radiation reflected from the substrate with a reference beam derived from the illumination beam to produce an output beam. Selecting a portion of the output beam. Measuring a spectrum of the received selected portion of the output beam. Determining reflectance properties of the target at the incidence angle from the measured spectrum.

According to a further embodiment of the present invention, there is provided a lithography apparatus comprising an exposure system and an inspection apparatus comprising: an illumination source configured to provide an illumination beam of broadband radiation, an interferometer configured to use the illumination beam to illuminate a target on a substrate at an incidence angle and to use radiation reflected from the substrate with a reference beam derived from the illumination beam to produce an output beam, a sampling device arranged to select a portion of the output beam, a spectrometer configured to receive the selected portion of the output beam and to measure a spectrum of the received selected portion of the output beam, and one or more processor configured to determine reflectance properties of the target at the incidence angle from the measured spectrum and to control the exposure system using the determined reflectance properties.

According to a still further embodiment of the present invention, there is provided lithographic cell comprising a lithographic apparatus comprising an exposure system and an inspection apparatus. The inspection apparatus comprises an illumination source configured to provide an illumination beam of broadband radiation, an interferometer configured to use the illumination beam to illuminate a target on a substrate at an incidence angle and to use radiation reflected from the substrate with a reference beam derived from the illumination beam to produce an output beam, a sampling device arranged to select a portion of the output beam, a spectrometer configured to receive the selected portion of the output beam and to measure a spectrum of the received selected portion of the output beam, and one or more processor configured to determine reflectance properties of the target at the incidence angle from the measured spectrum and to control the exposure system using the determined reflectance properties.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
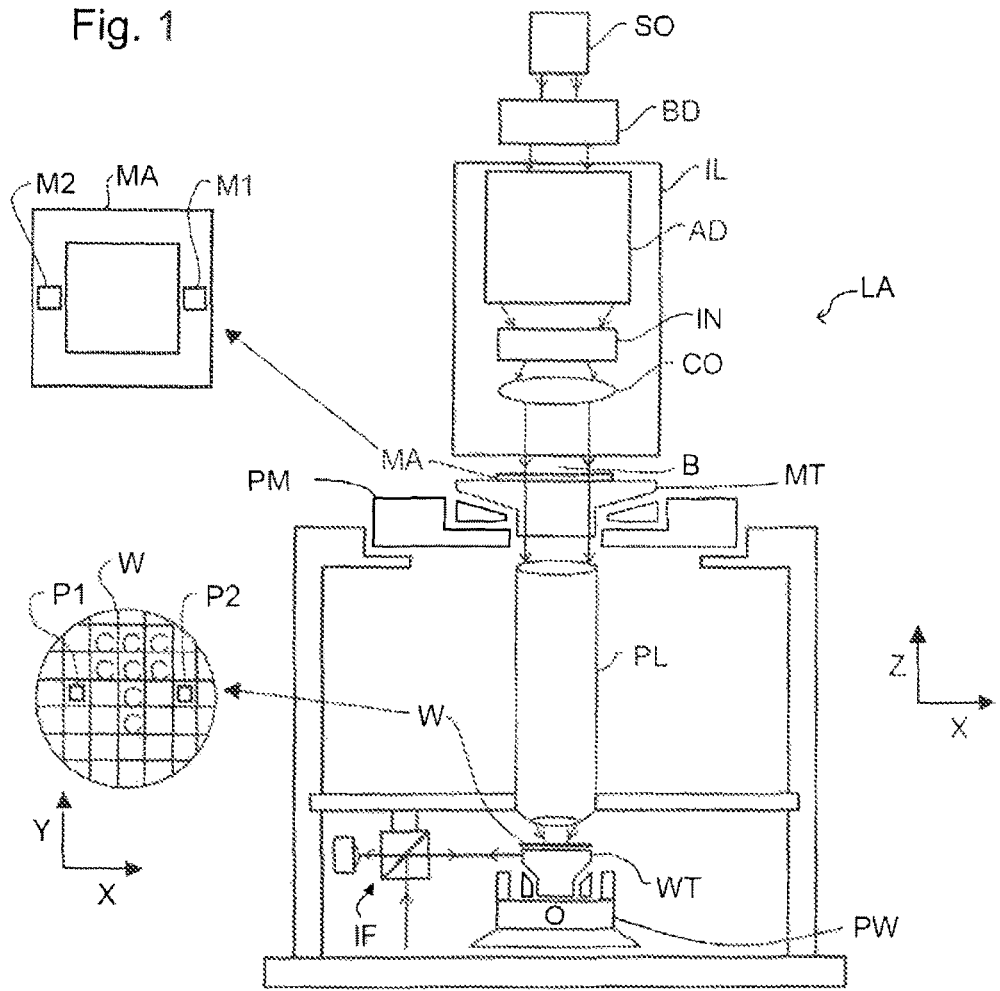
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features.

Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
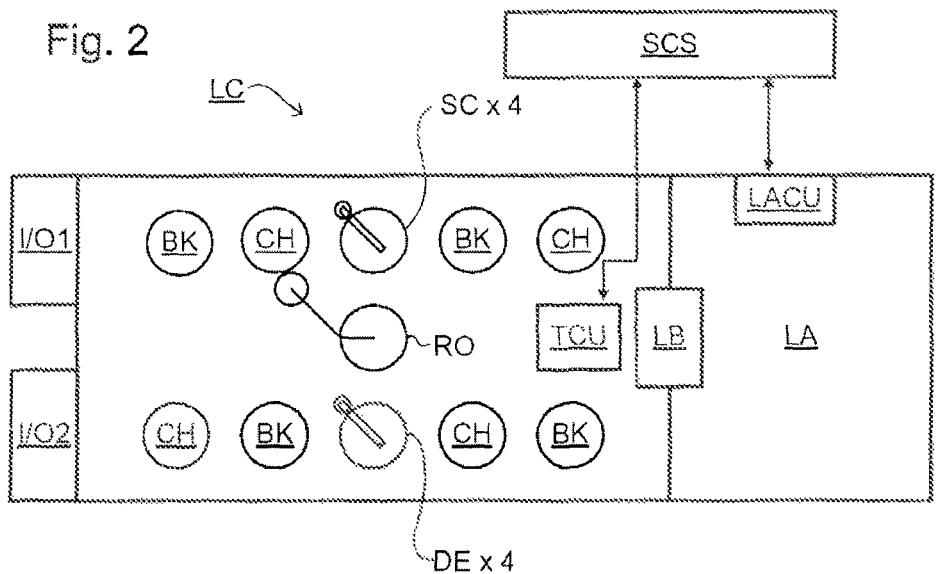
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
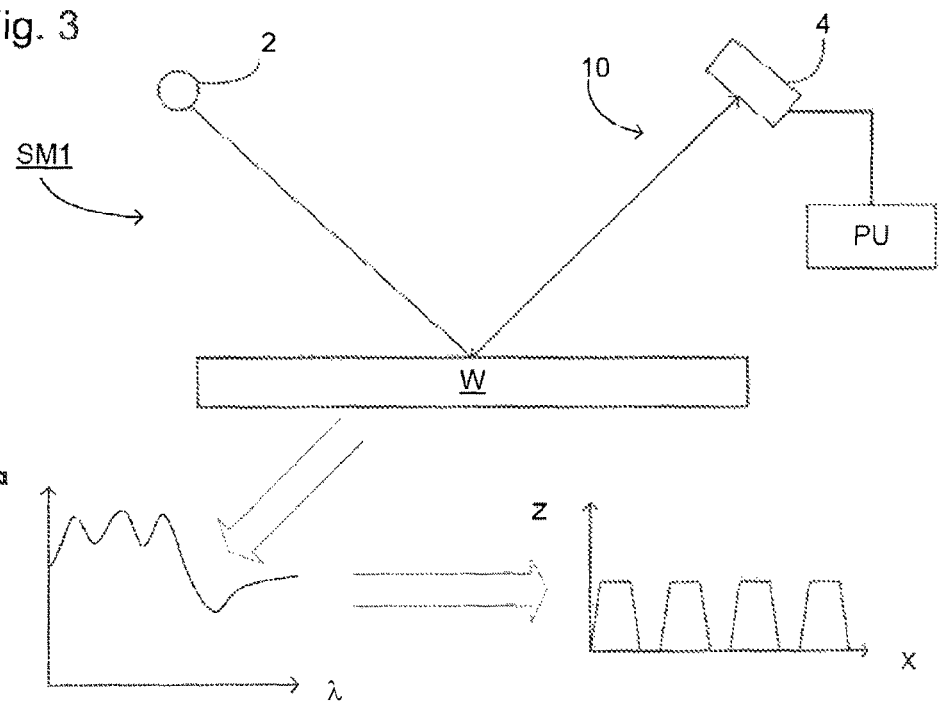
FIG. 3 depicts a first scatterometer.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
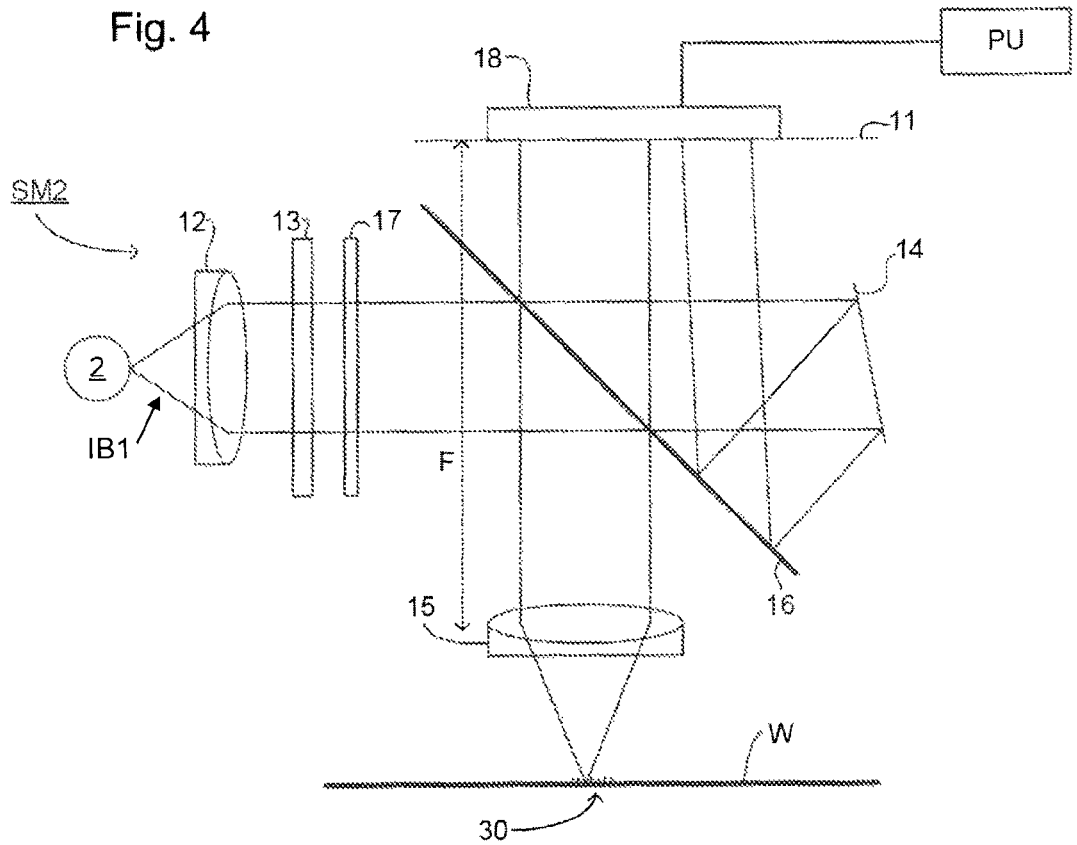
FIG. 4 depicts a second scatterometer.

Another scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern can be sensitive to lens aberrations of the project system PL in the lithographic projection apparatus, and illumination symmetry and the presence of these effects will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

U.S. Patent Application publication number US 2004/0085544 (A1), incorporated by reference herein in its entirely, discloses an example method including: imaging test light emerging from a test object over a range of angles to interfere with reference light on a detector, wherein the test and reference light are derived from a common source; for each of the angles, simultaneously varying an optical path length difference from the source to the detector between interfering portions of the test and reference light at a rate that depends on the angle at which the test light emerges from the test object; and determining an angle-dependence of an optical property of the test object based on the interference between the test and reference light as the optical path length difference is varied for each of the angles. However, that approach is that susceptible to vibration because the reference mirror is sequentially stepped and the "phase steps need to be accurately known. This implies the need for a very stable set-up. Any mechanical vibration may introduce phase errors. That approach may not be suitable for measuring small in-die targets since it measures in the back-focal plane of a lens Embodiments of the present invention relate to using an "angle-resolved" version of FD-OCT (Fourier Domain Optical Coherence Tomography).

FD-OCT is used in medical imaging applications and is described for example in the publication "Ultrahigh resolution Fourier domain optical coherence tomography", R. A. Leitgeb et al, 17 May 2004, Vol. 12, No. 10, Optics Express 2156, which is incorporated by reference herein in its entirety.

Figure 5:
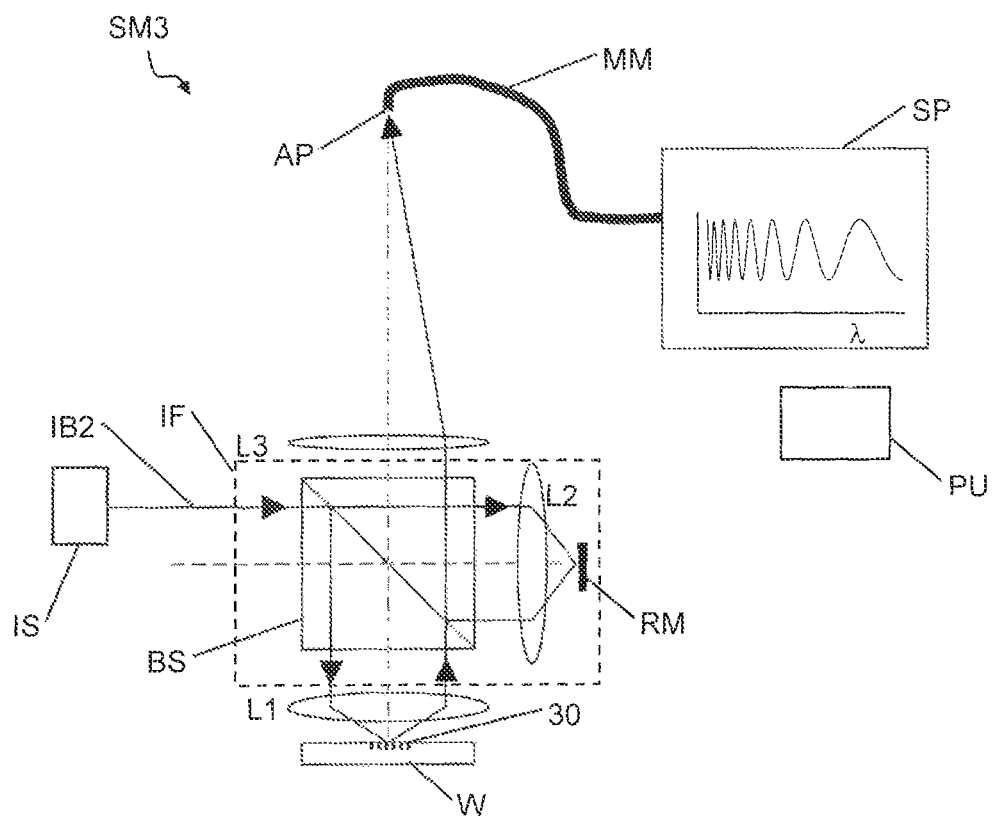
FIG. 5 depicts an inspection apparatus, in accordance with an embodiment.

FIG. 5 shows an embodiment using angle-resolved FD-OCT. A low-divergence broadband illumination beam IB2 from an illumination source IS is directed into an interferometer IF and split in two parts by beam splitter BS. The reflected part (measurement beam) is sent to a high NA (Numerical Aperture) objective L1 and is projected on the target 30 at a certain incidence angle. The transmitted part (reference beam) is projected on a reference mirror RM via lens L2. The lenses L1 and L2 should preferably be equal. If they are not equal then the different dispersion properties of L1 and L2 have to be accounted for. In that case the OPD gets an extra wavelength-dependent term that may be eliminated through a calibration.

The beams that are reflected by the reference mirror and reflected by the target are recombined by the beam splitter BS into an interferometer output beam. Lens L3 is used to make an image of the overlapping object and reference mirror on the input facet of a multimode detection fiber, thus serving as a sampling device. The size of the image of the target is larger than the fiber core diameter. In this way, the fiber acts as an aperture that only selects and collects radiation from the area of interest and blocks all other parts of the image, thus selecting a portion of the output beam. In practice the image on the fiber is a strongly magnified version of the object. As a result, the angle-of-incidence on the fiber input is well within the NA of the fiber (typically 0.22). For example, if the target size is 10×10 μm² and the fiber core diameter is 200 μm then a magnification factor of 40 will create an image of the target of 400×400 μm² which is larger than the core diameter. The NA of the light incident on the fiber will be $NA_{obj}/40 \approx 0.024$ which is much smaller than the NA of standard multimode fibers.

The light that is captured by the fiber is sent to a spectrometer and the detected spectrum is given by:

$$I(\lambda) = R_{obj} + R_{ref} + 2\sqrt{R_{obj}R_{ref}} \cos\left(2\pi \frac{OPD}{\lambda} + \varphi_{obj} - \varphi_{ref}\right)$$

In this equation $R_{obj}$ and $R_{ref}$ are, respectively, the DC intensity of the target object and reference arm waves, $\phi_{obj}$, and $\phi_{ref}$ are the phase of the object and reference waves and OPD is the Optical Path Difference between the object and reference waves. In FD-OCT this OPD is deliberately set to a relatively large value. As a result of the large OPD, the intensity varies periodically as a function of $1/\lambda$ so that a high-frequency fringe pattern on the spectrometer spectral output is observed. In order to explain the subsequent signal processing more clearly we can also rewrite the measured spectrum in a slightly different form:

$$I(\nu) = R_{obj} + R_{ref} + 2\sqrt{R_{obj}R_{ref}} \cos(2\pi\nu\tau + \phi_{obj} - \phi_{ref})$$

In this equation $\nu$ and $\tau$ are, respectively, the optical frequency of the light and the time-of-flight difference between the object and reference waves. This equation shows that the phase information of the object ($\phi_{obj}$) is encoded on a high-frequency carrier. The principle of FD OCT relies on the fact that the spectral amplitude of the reflected light equals the Fourier transform of the longitudinal sample structure.

An FFT (Fast Fourier Transform) of I(ν), for example performed by processing unit PU, yields a frequency spectrum consisting a DC term $R_{obj}+R_{ref}$ and a signal on a high frequency carrier. By demodulating the high frequency components with a Fourier Transform two signal intensity components can be extracted:

$$I_C(\theta,\lambda) = \sqrt{R_{obj}(\theta,\lambda)R_{ref}} \cos(\phi_{obj}(\theta,\lambda) - \phi_{ref})$$

$$I_S(\theta,\lambda) = \sqrt{R_{obj}(\theta,\lambda)R_{ref}} \sin(\phi_{obj}(\theta,\lambda) - \phi_{ref})$$

The component $I_C$ that is in phase with the original carrier is referred to as the in-phase component. The other component $I_S$, which is 90° ($\pi/2$ radians) "out-of-phase", is referred to as the quadrature component. The dependence of the phase $\phi_{obj}$ on wavelength and incidence angle (θ) is explicitly shown in the equations. From this signal processing the complex reflectance of the object can be determined for a given angle of incidence for example using processor unit PU. Processor unit PU may be incorporated into the spectrometer or outside it.

Beyond specular reflection from the target, higher orders diffracted from other areas of the target may end up being selectively collected by the fiber facet aperture. These higher diffraction orders will normally not interfere with the reference beam and as a result they will not contribute to the signal formation of the high-frequency carrier term.

The carrier frequency depends on the actual OPD so the actual frequency can be used for focus control. By including the phase of the carrier fine-focus control can be performed as well. This technique may therefore also be used as a level sensor. Level sensing can be implemented by simply putting an inspection apparatus such as described with reference to FIG. 5 in a lithography apparatus and using the phase of the measured high frequency carrier to measure the height of the substrate.

"Reflectance properties" referred to herein may be for example the raw spectrometer spectral data, the Fourier transformed data, the extracted intensity components or carrier phase or the calculated complex reflectance. The reflectance properties implicitly relate to a range of frequencies and may be representative of one or more incidence angles, as described below.

If the two lenses L1 and L2 are not identical, additional calibrations will be necessary to calibrate the different dispersion properties of the two lenses.

The incident light is normally polarized and it is also possible to measure the polarization state of the scattered light with a slight modification of the set-up. This can be performed by including an ellipsometry extension to the scatterometer such as described in U.S. Pat. No. 7,701,577, which is incorporated by reference herein in its entirety.

A series of signals may be measured for different angles of incidence. This can be done by scanning the illumination beam in the back-focal plane of L1. This scanning may be performed as described below with reference to FIG. 6.

Figure 6:
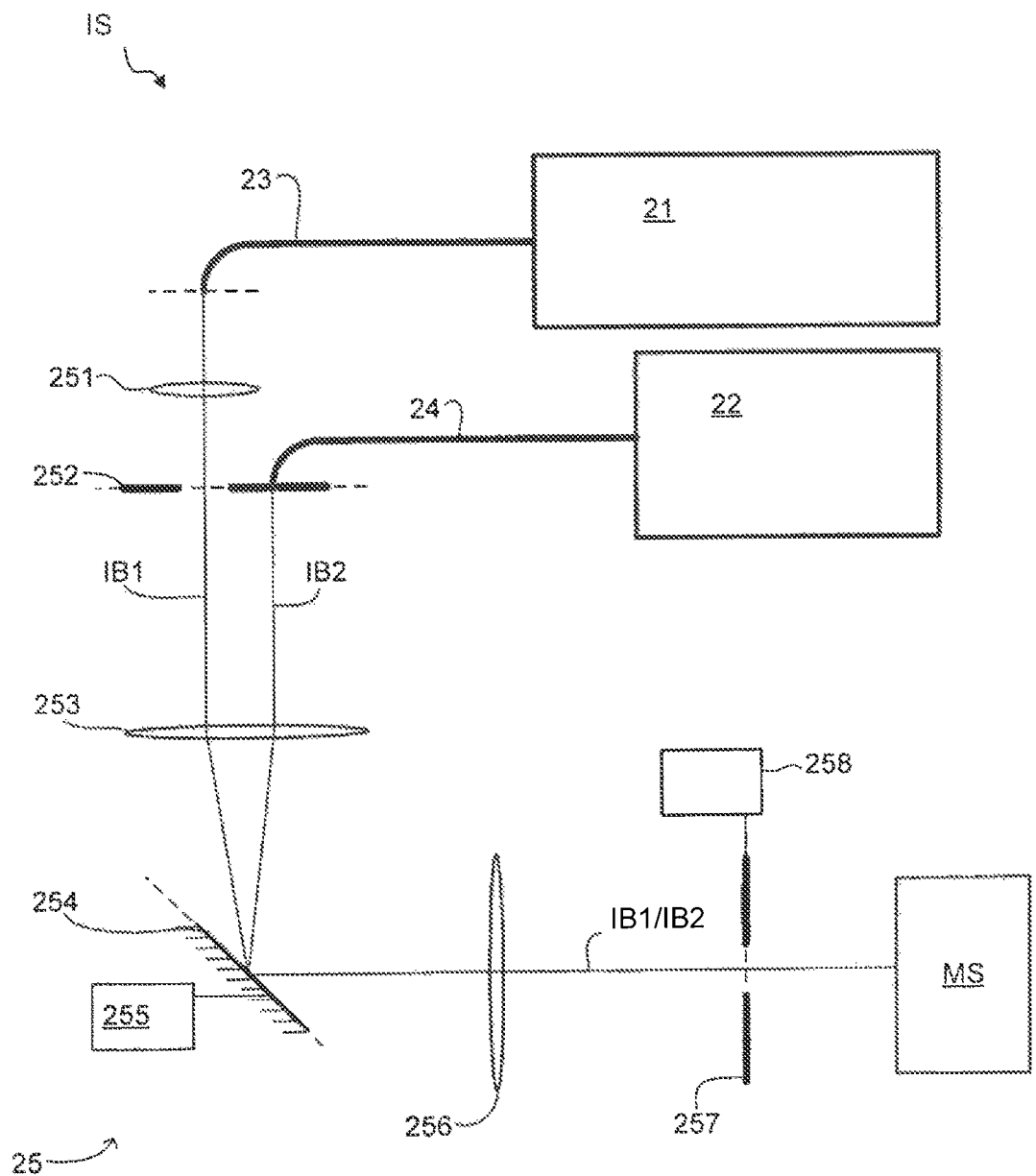
FIG. 6 depicts radiation source and beam deflection arrangements suitable for the inspection apparatus of FIG. 5.

The illumination source unit IS is shown in more detail in FIG. 6. The source unit provides illumination for two modes of operation of the scatterometer. The first mode is as an angle-resolved scatterometer using IB1 and measurement in the pupil plane, similar to as described with reference to FIG. 4. The second mode uses the FD-OCT approach using IB2 similar to as described with reference to FIG. 5.

The source includes a first source module 21, which may include for example a xenon lamp and provides a first illumination beam IB1, and a second source module 22, which provides a second illumination beam IB2. The second source module 22 may include a supercontinuum laser to provide a broadband (white light) output to form the second illumination beam IB2. A beam selection unit 25 directs the illumination beams to the remainder of the inspection apparatus, depicted MS in FIG. 6.

The supercontinuum laser may include a pulsed laser source whose output is fed into a non-linear medium, e.g., a photonic crystal fiber. The pulsed source emits very short pulses, e.g., of femtosecond or picosecond duration, of a narrow band of wavelengths which are spread by the non-linear medium into a broadband beam of radiation. This type of source can provide a powerful beam with a low etendue and a suitable range of wavelengths. Other sources are suitable, for example, a Xenon gas discharge (either electrical discharge or laser-produced plasma) or a Deuterium source in case of a broadband UV wavelength range.

Outputs of the first and second sources 21, 22 are conveniently led to the beam selection unit 25 by optical fibers 23 and 24. Fiber 23 may include a multimode fiber and fiber 24 may include an endlessly single-mode PM fiber.

The beam selection unit in this embodiment includes a tilting mirror 254 driven by actuator 255 to select one of the illumination beams IB1, IB2 for the output to the remainder of the inspection apparatus. The tilting mirror is positioned in a back-projected substrate plane, which is a plane conjugate with the substrate having the target being measured, created by an optical system including a first condensing lens 256. A second condensing lens 253 creates a back-projected pupil plane, which is a plane that is a Fourier transform of the back-projected substrate plane, in which is positioned an aperture plate 252. The aperture plate 252 has two apertures separated by a small distance. In one aperture, a secondary source is formed by a third condensing lens 251 which collects light from the first source 21 output by fiber 23. In the other aperture, the output of the fiber 24, carrying light from second source 22, is located.

With the above arrangement, the two illumination beams are brought together on the tilting mirror 254, but have different angle of incidence. Thus, by changing the angle of the tilting mirror 254 by only a small amount, e.g., less than 50 mrad in an embodiment, one of the illumination beams can be selected and directed along the axis of first condensing lens 256. The other beam is directed off-axis and blocked by an aperture stop 257 provided on a further back-projected pupil plane. Aperture stop 257 is preferably provided in a turret or carousel driven by actuator 258 so that a selected one of a plurality of apertures can be interposed into the optical path, in accordance with the illumination beam chosen.

It will appreciated that the above embodiment can readily be extended to encompass more than two light sources to provide additional flexibility. The spacing of the multiple sources in the aperture plate 252, the focal lengths of condenser lenses 256 and 253 and the range of movement of the tiltable mirror can be chosen to accommodate the desired number of sources.

Furthermore, as well as switching between illumination beams IB1, IB2, the tiltable mirror can be used, in combination with an appropriate aperture stop 257, to control the incidence angle of illumination at the wafer. The tiltable mirror may be tiltable about one or two axes. Preferably, to avoid positioning errors, the tiltable mirror pivots about the point of incidence of the illumination beams IB1, IB2.

The basic illumination arrangement of the metrology device is Kohler illumination so that the source size and angular distribution in the back-projected pupil plane at aperture plate 252 respectively determine the angular distribution of illumination and spot size on the substrate. Thus, the illustrated arrangement allows for rapid switching between a mode with illumination of a small area from a wide range of angles, using the first source module, and mode with illumination of a larger area from a narrow range of angles, using the second source module. In the latter mode, by use of a sufficiently powerful source and a rapidly tiltable mirror, a large number of FD-OCT measurements using the second illumination beam IB2 at different angles of illumination can be taken in a short period of time.

In an embodiment, a small measurement spot may be provided to underfill relatively large targets, e.g., in the scribe line, for accurate measurements as an angle-resolved scatterometer using IB1 and measurement in the pupil plane, similar to as described with reference to FIG. 4, and whilst a larger spot with a well defined illumination incidence angle may be provided for measurements using IB2 of relatively small targets, e.g., in-die markers, using the FD-OCT method similar to as described with reference to FIG. 5.

The two sources may both be kept on during use of the apparatus to allow rapid selection between them or selectively energized as required.

Figure 7:
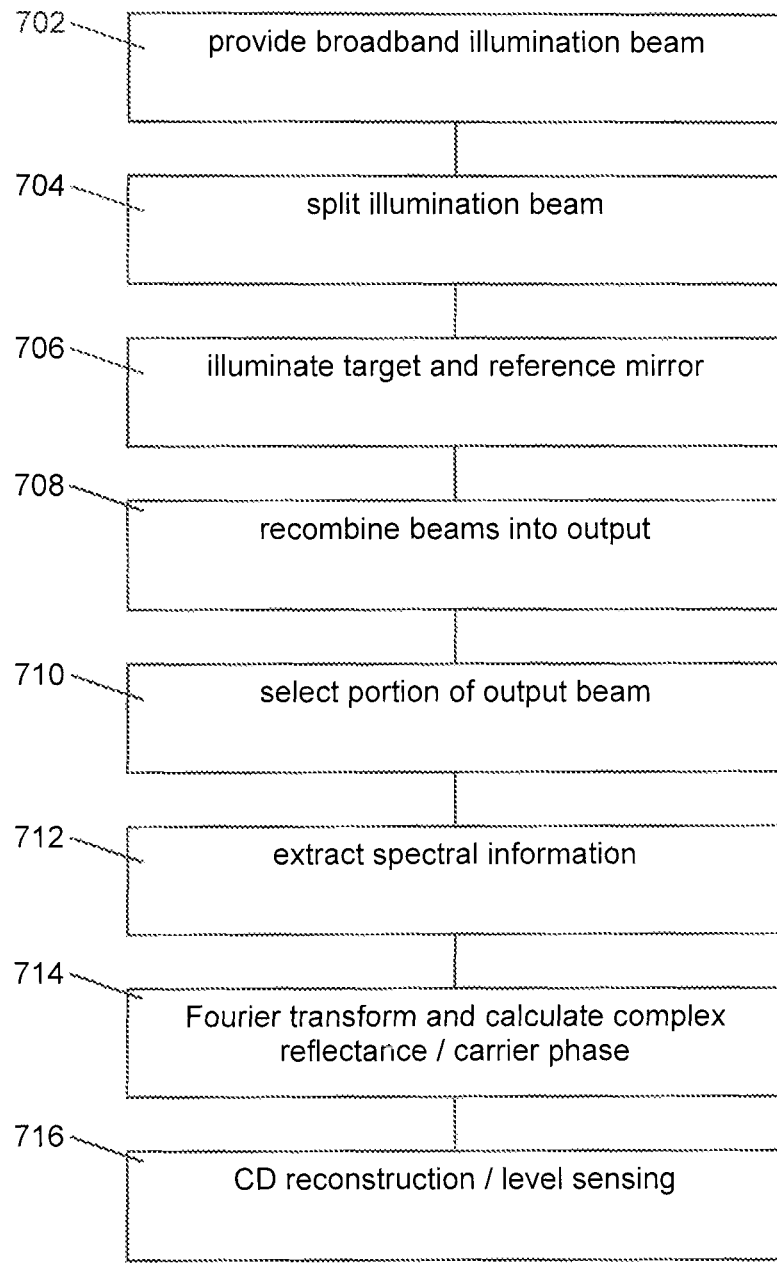
FIG. 7 depicts a method of inspection, in accordance with an embodiment.

FIG. 7 is a flow chart of a method according to an embodiment. The method has the steps as follows:

702: Provide a broadband illumination beam.

704: Split the illumination beam into measurement and reference beams.

706: Illuminate the target with the measurement beam at the incidence angle and the reference mirror with the reference beam.

708: Recombine the reflected portion of the measurement beam and the reference beam into an output beam.

710: Select a portion of the output beam, for example using an aperture.

712: Measure spectrum of the selected portion of the output beam to extract spectral information from it.

714: Fourier transform and calculate complex reflectance and/or carrier phase.

716: Determine CD by reconstruction using complex reflector or determine the wafer surface height using carrier phase.

A processor such as PU in FIG. 5 may be used to control for example focus or dose settings of an exposure system of a lithographic apparatus by using the determined reflectance properties and reconstructed CD and/or level sensing measurements. The inspection apparatus may be incorporated in a lithographic apparatus or lithographic cell.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In the embodiments described herein, the reflectance properties of the target are similarly calculated. Target shape information can be obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using an inspection apparatus as described with reference to FIG. 5 in combination with modeling of a target structure such as the target 30 and its reflectance properties, measurement of the shape and other parameters of the structure can be performed in a number of ways. In a first type of process, represented by FIG. 8, reflectance properties based on a first estimate of the target shape (a first candidate structure) is calculated and compared with the observed reflectance properties. Parameters of the model are then varied systematically and the reflectance properties re-calculated in a series of iterations, to generate new candidate structures and so arrive at a best fit. In a second type of process, represented by FIG. 9, reflectance properties for many different candidate structures are calculated in advance to create a 'library' of sets of reflectance properties. Then the reflectance properties observed from the measurement target is compared with the library of calculated reflectance properties to find a best fit. Both methods can be used together: a coarse fit can be obtained from a library, followed by an iterative process to find a best fit.

Figure 8:
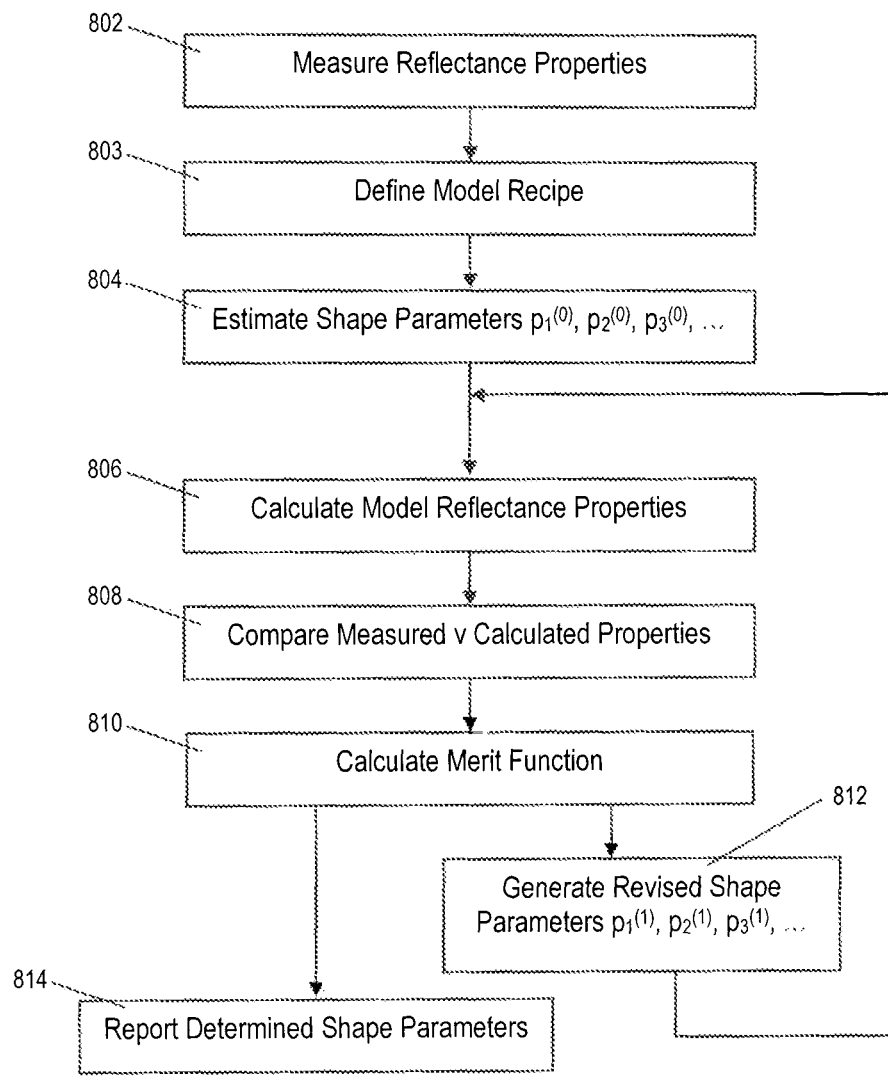
FIG. 8 depicts a first example process for reconstruction of a structure from reflectance properties measurements.

Referring to FIG. 8 in more detail, the way the measurement of the target shape and/or material properties is carried out will be described in summary. The target will be assumed for this description to be periodic in only 1 direction (1-D structure). In practice it may be periodic in 2 directions (2-dimensional structure), and the processing will be adapted accordingly.

802: The reflectance properties of the actual target on the substrate are measured using a scatterometer such as described above with reference to FIG. 5. This measured reflectance properties are forwarded to a calculation system such as a computer. The calculation system may be the processing unit PU of FIG. 5 referred to above, or it may be a separate apparatus.

803: A 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, we shall introduce ways in which parameters can be permitted to vary without being fully independent floating parameters. For the purposes of describing FIG. 8, only the variable parameters are considered as parameters $p_i$.

804: A model target shape is estimated by setting initial values $p_i^{(0)}$ for the floating parameters (i.e., $p_1^{(0)}$, $p_2^{(0)}$, $p_3^{(0)}$ and so on). Each floating parameter will be generated within certain predetermined ranges, as defined in the recipe.

806: The parameters representing the estimated shape, together with the optical properties of the different elements of the model, are used to calculate the reflectance properties, for example using a rigorous optical diffraction method such as RCWA or any other solver of Maxwell equations. This gives estimated or model reflectance properties of the estimated target shape.

808, 810: The measured reflectance properties and the model reflectance properties are then compared and their similarities and differences are used to calculate a "merit function" for the model target shape.

812: Assuming that the merit function indicates that the model needs to be improved before it represents accurately the actual target shape, new parameters p1(1), p2(1), p3(1), etc. are estimated and fed back iteratively into step 806. Steps 806-812 can be repeated.

In order to assist the search, the calculations in step 806 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

814: When the merit function indicates that this iterative process has converged on a solution with a desired accuracy, the currently estimated parameters are reported as the determined shape parameters of the actual target structure.

The computation time of this iterative process is largely determined by the forward diffraction model used, i.e., the calculation of the estimated model reflectance properties using a rigorous optical diffraction theory from the estimated target structure. If more parameters are required, then there are more degrees of freedom. The calculation time increases in principle with the power of the number of degrees of freedom. The estimated or model reflectance properties calculated at 806 can be expressed in various forms. Comparisons are simplified if the calculated pattern is expressed in the same form as the measured reflectance properties generated in step 802. For example, a modeled spectrometer output spectrum can be compared easily with a raw spectrometer spectrum measured by the spectrometer of FIG. 5 or a modeled complex reflectance can be compared easily with a complex reflectance output from the processing unit PU of FIG. 5.

Figure 9:
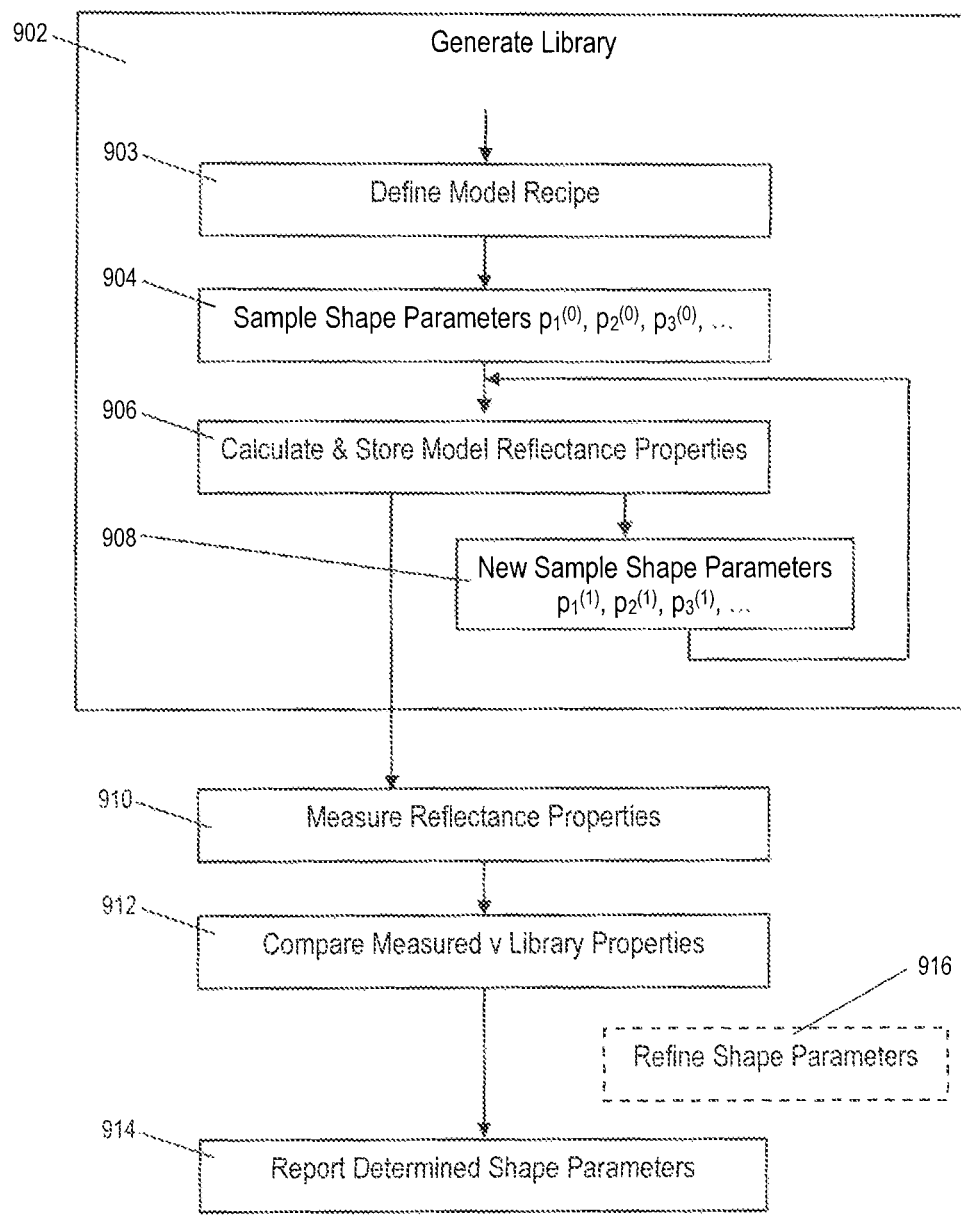
FIG. 9 depicts a second example process for reconstruction of a structure from reflectance properties measurements.

FIG. 9 illustrates an alternative example process in which plurality of model reflectance properties for different estimated target shapes (candidate structures) are calculated in advance and stored in a library for comparison with a real measurement. The underlying principles and terminology are the same as for the process of FIG. 8. The steps of the FIG. 9 process are:

902: The process of generating the library begins. A separate library may be generated for each type of target structure. The library may be generated by a user of the measurement apparatus according to need, or may be pre-generated by a supplier of the apparatus.

903: A 'model recipe' is established which defines a parameterized model of the target structure in terms of a number of parameters pi (p1, p2, p3 and so on). Considerations are similar to those in step 803 of the iterative process.

904: A first set of parameters p1(0), p2(0), p3(0), etc. is generated, for example by generating random values of all the parameters, each within its expected range of values.

906: Sets of model reflectance properties are calculated and stored in a library, representing the reflectance properties expected from a target shape represented by the parameters.

908: A new set of shape parameters $p_1^{(1)}, p_2^{(1)}, p_3^{(1)}$, etc. is generated. Steps 906-908 are repeated tens, hundreds or even thousands of times, until the library which comprises all the stored modeled sets of reflectance properties is judged sufficiently complete. Each stored pattern represents a sample point in the multi-dimensional parameter space. The samples in the library should populate the sample space with a sufficient density that any real set of reflectance properties will be sufficiently closely represented.

910: After the library is generated (though it could be before), the real target 30 is placed in the scatterometer and its reflectance properties are measured.

912: The measured reflectance properties are compared with the modeled sets of reflectance properties stored in the library to find the best matching pattern. The comparison may be made with every sample in the library, or a more systematic searching strategy may be employed, to reduce computational burden.

914: If a match is found then the estimated target shape used to generate the matching library reflectance properties can be determined to be the approximate object structure. The shape parameters corresponding to the matching sample are output as the determined shape parameters. The matching process may be performed directly on the model reflectance properties, or it may be performed on substitute models which are optimized for fast evaluation.

916: Optionally, the nearest matching sample is used as a starting point, and a refinement process is used to obtain the final parameters for reporting. This refinement process may comprise an iterative process very similar to that shown in FIG. 8, for example.

Whether refining step 916 is needed or not is a matter of choice for the implementer. If the library is very densely sampled, then iterative refinement may not be needed because a good match will always be found. On the other hand, such a library might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated reflectance properties and associated refined parameter sets as new entries in the library. In this way, a library can be used initially which is based on a relatively small amount of computational effort, but which builds into a larger library using the computational effort of the refining step 916. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward reflectance properties model at steps 806 and 906, i.e., the calculation of the estimated model reflectance properties using a rigorous optical diffraction theory from the estimated target shape.

Embodiments of the present invention provides several advantages:

1. Fast CD metrology on small grating is enabled.
2. Stray light that may occur in the sensor optics is effectively suppressed since it will have a significantly different OPD than the nominal OPD of the object. As a result it is effectively suppressed in the demodulation of the carrier frequency.
3. Phase-as-a-function-of-wavelength information is measured.
4. The measured signal also contains focus information that can be used for focus control (it obviates the need for an extra focus measuring branch).
5. This technique can also be used a level sensor.
6. Mixing with a strong reference wave of the object is also beneficial for measuring on objects with a low reflectance like a-C (amorphous carbon) films.

Although specific reference may be made in this text to the use of lithographic apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The descriptions above are intended to be illustrative, not limiting. Thus, it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection apparatus comprising:
    an illumination source configured to provide an illumination beam of broadband radiation;
    an interferometer configured to use the illumination beam to illuminate a target on a substrate at an incidence angle and to use radiation reflected from the substrate with a reference beam derived from the illumination beam to produce an output beam;
    an optical fiber configured to receive the output beam, wherein a core diameter of the optical fiber is arranged to select a portion of the output beam;
    a spectrometer configured to receive the selected portion of the output beam and to measure a spectrum of the received selected portion of the output beam; and
    a processor configured to determine reflectance properties of the target at the incidence angle from the measured spectrum.

2. The inspection apparatus of claim 1, wherein the illumination source is configured to adjust the incidence angle and the processor is configured to determine reflectance properties of the target at a plurality of incidence angles.

3. The inspection apparatus of claim 2, wherein the illumination source is configured to translate the illumination beam with respect to a pupil plane of the objective to adjust the incidence angle.

4. The inspection apparatus of claim 1, wherein the processor is configured to determine the reflectance properties by performing a Fourier transform of the measured spectrum.

5. The inspection apparatus of claim 1, wherein the processor is configured to determine the reflectance properties by calculating intensity and phase of the output beam as a function of frequency at the incidence angle.

6. The inspection apparatus of claim 1, wherein the processor is configured to determine the phase of a carrier signal from the measured spectrum and to determine a surface height of the substrate from the determined phase.

7. The inspection apparatus of claim 1, wherein the interferometer comprises:
    a beam splitter configured to split the illumination beam into a reference beam of radiation and a measurement beam of radiation;
    a reference arm configured to convey the reference beam;
    an objective configured to direct the measurement beam onto the target at the incidence angle; and
    a combiner configured to recombine the measurement beam reflected from the target with the reference beam from the reference arm into the output beam.

8. The inspection apparatus of claim 1, wherein the sampling device is located at an intermediate image of the target.

9. The inspection apparatus of claim 1, wherein the sampling device comprises an aperture.

10. An inspection method comprising:
    using an illumination beam to illuminate a target on a substrate at an incidence angle;
    using radiation reflected from the substrate with a reference beam derived from the illumination beam to produce an output beam;
    using an optical fiber having a core diameter that selects a portion of the output beam;
    measuring a spectrum of the received selected portion of the output beam; and
    determining reflectance properties of the target at the incidence angle from the measured spectrum.

11. The inspection method of claim 10, further comprising adjusting the incidence angle and determining reflectance properties of the target at a plurality of incidence angles.

12. The inspection method of claim 10, further comprising determining the reflectance properties by performing a Fourier transform of the measured spectrum.

13. The inspection method of claim 10, further comprising determining the reflectance properties by calculating intensity and phase of the output beam as a function of frequency at the incidence angle.

14. The inspection method of claim 10, further comprising determining the phase of a carrier signal from the measured spectrum and determining a surface height of the substrate from the determined phase.

15. The inspection method of claim 10, wherein the using the illumination beam to illuminate the target and the using radiation reflected from the substrate with a reference beam derived from the illumination beam to produce an output beam comprise:
    splitting the illumination beam into a reference beam of radiation and a measurement beam of radiation;
    conveying the reference beam along a reference arm;
    directing the measurement beam onto the target at the incidence angle; and recombining the measurement beam reflected from the target with the reference beam from the reference arm into the output beam.

16. The inspection method of claim 10, comprising translating the illumination beam with respect to a pupil plane of the objective to adjust the incidence angle.

17. The inspection method of claim 10, comprising selecting a portion of the output beam at an intermediate image of the target.

18. The inspection method of claim 10, comprising selecting a portion of the output beam with an aperture.

19. A lithography apparatus comprising:
an exposure system; and
an inspection apparatus comprising:
   an illumination source configured to provide an illumination beam of broadband radiation;
   an interferometer configured to use the illumination beam to illuminate a target on a substrate at an incidence angle and to use radiation reflected from the substrate with a reference beam derived from the illumination beam to produce an output beam;
   an optical fiber configured to receive the output beam, wherein a core diameter of the optical fiber is arranged to select a portion of the output beam;
   a spectrometer configured to receive the selected portion of the output beam and to measure a spectrum of the received selected portion of the output beam; and
   one or more processor configured to determine reflectance properties of the target at the incidence angle from the measured spectrum and to control the exposure system using the determined reflectance properties.

20. A lithographic cell comprising
a lithographic apparatus comprising an exposure system; and
an inspection apparatus comprising:
   an illumination source configured to provide an illumination beam of broadband radiation;
   an interferometer configured to use the illumination beam to illuminate a target on a substrate at an incidence angle and to use radiation reflected from the substrate with a reference beam derived from the illumination beam to produce an output beam;
   an optical fiber configured to receive the output beam, wherein a core diameter of the optical fiber is arranged to select a portion of the output beam;
   a spectrometer configured to receive the selected portion of the output beam and to measure a spectrum of the received selected portion of the output beam; and
   one or more processor configured to determine reflectance properties of the target at the incidence angle from the measured spectrum and to control the exposure system using the determined reflectance properties.

\* \* \* \* \*